US008795168B2

(12) United States Patent
Goh et al.

(10) Patent No.: US 8,795,168 B2
(45) Date of Patent: Aug. 5, 2014

(54) METHOD AND SYSTEM FOR CAPTURING AND MONITORING A PHYSIOLOGICAL PARAMETER AND MOVEMENT WITHIN AN AREA OF AT LEAST ONE PERSON

(75) Inventors: Zenton Goh, Singapore (SG); Sian Sheng Neo, Singapore (SG); Hon Cheong Ng, Singapore (SG); Soh Min Lim, Singapore (SG)

(73) Assignee: Cadi Scientific Pte Ltd., Singapore (SG)

( * ) Notice: Subject to any disclaimer, the term of this patent is extended or adjusted under 35 U.S.C. 154(b) by 331 days.

(21) Appl. No.: 10/564,493

(22) PCT Filed: Jul. 17, 2003

(86) PCT No.: PCT/SG03/00171
§ 371 (c)(1),
(2), (4) Date: Jan. 12, 2006

(87) PCT Pub. No.: WO2005/006970
PCT Pub. Date: Jan. 27, 2005

(65) Prior Publication Data
US 2006/0178567 A1    Aug. 10, 2006

(51) Int. Cl.
*A61B 5/00* (2006.01)
*G01S 5/02* (2010.01)
*A61B 5/01* (2006.01)
*G06F 19/00* (2011.01)
*G01S 5/00* (2006.01)

(52) U.S. Cl.
CPC ............ *G06F 19/3418* (2013.01); *G06F 19/30* (2013.01); *G06F 19/3493* (2013.01); *G01S 5/0009* (2013.01); *G01S 5/0018* (2013.01); *G01S 5/0294* (2013.01); *G01S 5/0231* (2013.01); *A61B 5/0002* (2013.01); *A61B 5/0015* (2013.01); *A61B 5/01* (2013.01); *A61B 2562/08* (2013.01); *Y10S 128/903* (2013.01); *Y10S 128/904* (2013.01); *Y10S 128/92* (2013.01)
USPC ........... 600/301; 600/549; 128/903; 128/904; 128/920; 705/2; 705/3; 340/7.27; 340/8.1; 340/539.12; 340/870.01; 340/870.16

(58) Field of Classification Search
USPC .................. 600/300, 301; 128/903–905, 920
See application file for complete search history.

(56) References Cited

U.S. PATENT DOCUMENTS 3,943,918 A * 3/1976 Lewis ............................ 600/392
4,321,933 A * 3/1982 Baessler ....................... 600/549
(Continued)

FOREIGN PATENT DOCUMENTS

EP         1123685 A1    8/2001
JP         6242206 A     9/1994
(Continued)

*Primary Examiner* — Gary Jackson
*Assistant Examiner* — Marie Archer
(74) *Attorney, Agent, or Firm* — Hultquist, PLLC; Steven J. Hultquist; Mary B. Grant

(57) ABSTRACT

A method for capturing and monitoring at least one physiological parameter and movement within an area of at least one person are disclosed. The area is divided into cells having respective location identifiers. Each person is provided with a respective device for measuring at least one physiological parameter of the person. The physiological parameter is indicative of whether the person has a physical condition. Each device has a device identifier. The device is used to at least intermittently measure a physiological parameter of the person using the respective device to obtain a physiological parameter reading for each measurement. The physiological parameter reading is associated with the respective device identifier of the device by which, the respective location identifier of the cell in which, and a time at which the physiological parameter reading is obtained. The associated information is stored at a remote location. A system and a physiological parameter device are also disclosed.

20 Claims, 6 Drawing Sheets

(56) References Cited

U.S. PATENT DOCUMENTS

| | | | |
|---|---|---|---|
| 4,747,413 A * | 5/1988 | Bloch | 600/549 |
| 4,958,645 A * | 9/1990 | Cadell et al. | 600/484 |
| 5,153,584 A * | 10/1992 | Engira | 340/870.18 |
| 5,365,217 A * | 11/1994 | Toner | 340/539.11 |
| 5,458,123 A * | 10/1995 | Unger | 600/509 |
| 5,748,103 A * | 5/1998 | Flach et al. | 340/870.07 |
| 6,072,396 A * | 6/2000 | Gaukel | 340/573.4 |
| 6,102,856 A * | 8/2000 | Groff et al. | 600/301 |
| 6,238,337 B1 * | 5/2001 | Kambhatla et al. | 600/300 |
| 6,416,471 B1 * | 7/2002 | Kumar et al. | 600/300 |
| 6,529,164 B1 * | 3/2003 | Carter | 342/463 |
| 6,579,231 B1 * | 6/2003 | Phipps | 600/300 |
| 6,589,170 B1 | 7/2003 | Flach et al. | |
| 6,856,832 B1 * | 2/2005 | Matsumura et al. | 600/523 |
| 6,870,484 B1 * | 3/2005 | Brinsfield et al. | 340/8.1 |
| 6,894,975 B1 * | 5/2005 | Partyka | 370/235 |
| 6,897,788 B2 * | 5/2005 | Khair et al. | 340/870.16 |
| 6,970,097 B2 * | 11/2005 | Welles et al. | 340/8.1 |
| 6,982,639 B2 * | 1/2006 | Brackett et al. | 340/539.13 |
| 7,109,859 B2 * | 9/2006 | Peeters | 340/539.11 |
| 7,218,938 B1 * | 5/2007 | Lau et al. | 455/456.1 |
| 7,993,266 B2 * | 8/2011 | Colston et al. | 600/300 |
| 2002/0013518 A1 | 1/2002 | Colquitt et al. | |
| 2003/0009154 A1 * | 1/2003 | Whitman | 606/1 |
| 2003/0181815 A1 * | 9/2003 | Ebner et al. | 600/483 |
| 2003/0216625 A1 * | 11/2003 | Phipps | 600/300 |
| 2004/0059205 A1 * | 3/2004 | Carlson et al. | 600/310 |
| 2004/0073093 A1 * | 4/2004 | Hatlestad | 600/300 |
| 2005/0094705 A1 * | 5/2005 | Chi | 374/121 |

FOREIGN PATENT DOCUMENTS

| | | |
|---|---|---|
| JP | 10-155748 A | 6/1998 |
| JP | 11-070086 A | 3/1999 |
| JP | 2000-074745 A | 3/2000 |
| JP | 2003-006342 A | 1/2003 |
| JP | 2003-050867 A | 2/2003 |
| WO | 9006090 A1 | 6/1990 |

* cited by examiner

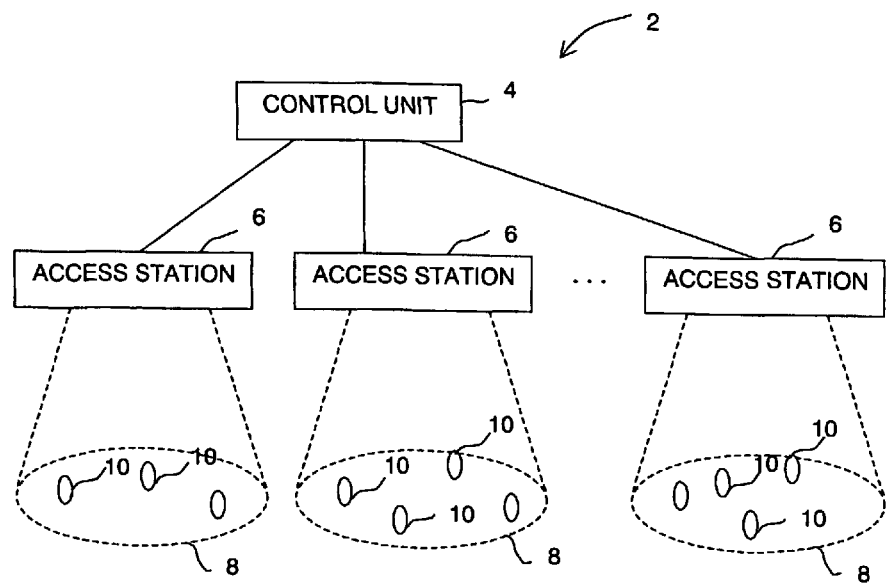

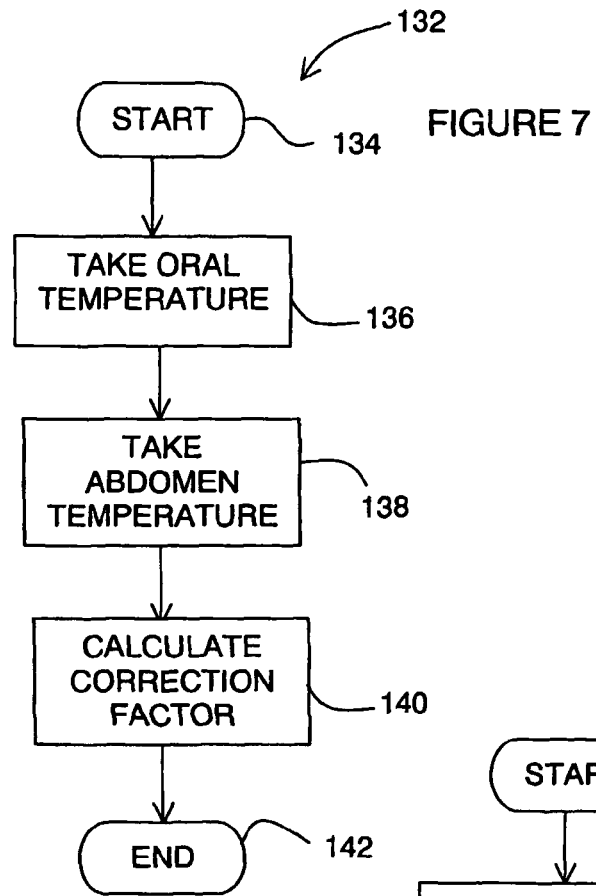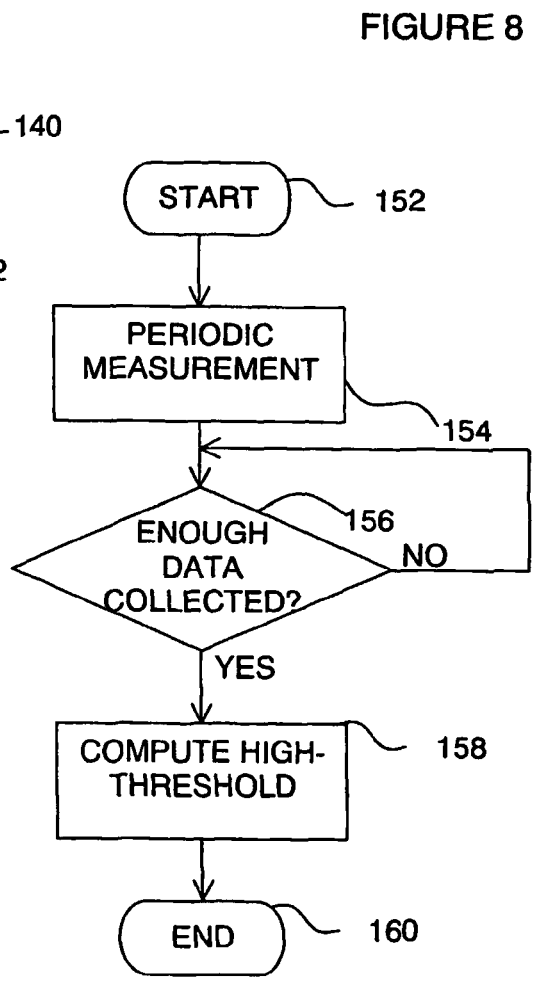

METHOD AND SYSTEM FOR CAPTURING AND MONITORING A PHYSIOLOGICAL PARAMETER AND MOVEMENT WITHIN AN AREA OF AT LEAST ONE PERSON

CROSS-REFERENCE TO RELATED APPLICATION

This application is filed under the provisions of 35 U.S.C. §371 and claims benefit of the priority of International Patent Application No. PCT/SG2003/000171 filed Jul. 17, 2003. The disclosure of said International Patent Application is hereby incorporated herein by reference, in its entirety, for all purposes.

BACKGROUND

This invention relates to a method and a system of tracking movement of a group of people in an area so that when a person in the group is detected to have a physical condition, the person may be located.

The severe acute respiratory syndrome (SARS) is an infectious disease. People who are suspected of having contracted SARS needs to be urgently identified, located and isolated to prevent the spreading of the disease to other people. One of the symptoms of SARS is fever. Consequently, it has become important for monitoring the body temperature of people to determine if they run a temperature, i.e. they have a fever.

Typically, people visiting a building such as an office building or a hospital are required to have their body temperatures taken at the entrance of the building. If the body temperature of a particular person is found to be above a pre-determined threshold, the person may be barred from entering the building, and may be asked instead to consult a doctor. Such a one-time measurement of body temperature may not be ideal.

For example, a person may have a normal body temperature when entering the building. However, the person may subsequently develop a fever after entering the building. And if the person has contracted the SARS virus and remains in the building for hours, he may potentially infect the other people in the building by passing the virus to them. Such a situation may result in a large cluster of SARS infected people and thus poses a serious health threat.

Another reason why a one-time measurement of body temperature is not ideal is because not everyone has the exact same temperature. The normal body temperature of a person varies depending on age, gender, recent activity, food and fluid consumption, time of day, etc., and for women, the stage of a menstrual cycle. The body temperature of a person at a particular time also varies when taken from different parts of the body. A normal body temperature can range from 36.5° C. to 37.2° C. However, a threshold of 37.8° C. is often used for deciding if a person has fever. The use of such a fixed threshold is not ideal because about 5% of the population is known to have a body temperature that falls outside the normal range. Using the single fixed threshold to gauge if a person has fever will cause those having a body temperature higher than that in the range to be wrongly diagnosed to have fever, thereby causing them unnecessary inconvenience and distress. What may be worse is that using such a fixed threshold may not be able to detect fever in people with a normal temperature lower than that in the range. In other words, real cases of fever may not be detectable.

SUMMARY

According to an aspect of the invention, there is provided a method of capturing and monitoring at least one physiological parameter and movement within an area of at least one person. The method includes dividing the area into cells having respective location identifiers and providing each person with a respective device for measuring at least one physiological parameter of each person. The physiological parameter is indicative of whether the person has a physical condition. Each device has a device identifier. The method further includes at least intermittently measuring a physiological parameter of the at least one person using the respective device to obtain a physiological parameter reading for each measurement. The method also includes associating each of at least a selected number of physiological parameter readings with the respective device identifier of the device by which, and the respective location identifier of the cell in which, a time at which the physiological parameter reading is obtained. The method further includes storing the associated physiological parameter reading, device identifier, location identifier and time.

The monitoring may be carried out from a remote location. The method may then include transmitting the associated physiological parameter reading, device identifier, location identifier and time to the remote location prior to storing them thereat.

According to one embodiment, dividing an area into cells involves a deployment of access stations at different locations in a building. Each of the access stations has a respective station identifier that serves as a location identifier. When the device obtains a physiological parameter reading, the device transmits the reading along with the respective device identifier. If the device is within a cell, the access station of the cell is able to receive the reading and device identifier and associate them with the respective station identifier. The access station subsequently transmits the associated reading, device identifier, station identifier to a remote control unit for storage thereon. The remote control unit further associates a time with the reading, device identifier and station identifier received from the access station. The time may also include a date. This embodiment of the invention will be described in detail later.

The method may further include comparing the physiological parameter reading with a first predetermined physiological parameter threshold value to determine if the person is wearing the device properly. In such a case, the method may further include identifying and locating the person using the device identifier and the location identifier associated with the physiological parameter reading if the person is determined not to be wearing the device properly.

The method may also include comparing the physiological parameter reading with a second predetermined physiological parameter threshold value to determine if the person has a physical condition. In such a case, the method further includes identifying and locating the at least one person using the device identifier and the location identifier associated with the physiological parameter reading if the person is determined to have the physical condition. The second predetermined physiological parameter threshold value may be predetermined individually.

The method may include adjusting the physiological parameter reading by a physiological parameter correction factor that is individually determined for the at least one person prior to comparing the adjusted physiological parameter reading with the first or the second predetermined physiological parameter threshold value.

The method may further include matching a time and location identifier associated with at least one physiological parameter reading taken from a respective device of at least one other person with those of the identified and located person and identifying the at least one other person to have been in physical proximity of the identified and located person if there is a match.

According to another aspect of the invention, there is provided a system for implementing the method according to the above described embodiment. The system includes a remote control unit and two or more access stations provided in a spatial arrangement within the area. Such an arrangement thereby divides the area into respective cells. Each access station has a respective station identifier, is being connected to the control unit and is adapted to receive a physiological parameter reading and a respective device identifier from at least one physiological parameter measuring device attached to a first person. The access station transmits the received physiological parameter reading and the device identifier along with its station identifier to the control unit. The associated information and a time at which the physiological parameter reading is obtained by the device is stored in a first record at the remote control unit.

The control unit may be adapted to compare the physiological parameter reading with a first predetermined physiological parameter threshold value to determine if the first person is wearing the device properly. The control unit may further be adapted to provide information corresponding to the device identifier and the location identifier associated with the physiological parameter reading for identifying and locating the first person if the first person is determined not to be wearing the device properly.

The control unit may also be adapted to compare the physiological parameter reading with a second predetermined threshold value to determine if the first person has a physical condition. The control unit may be further adapted to provide information corresponding to the device identifier and the location identifier associated with the physiological parameter reading for identifying and locating the first person if the first person is to have the physical condition. The second predetermined physiological parameter threshold may be predetermined individually for the first person.

The control unit may be adapted to match a time and location identifier of at least another record obtained from another respective device of at least one other person with those in the first record and to identify the other person to have been in physical proximity of the first person if there is a match.

The physiological parameter reading may be adjusted to include a physiological parameter correction factor that is individually determined for the first person prior to comparing the adjusted physiological parameter reading with either the first or second physiological parameter threshold value.

The control unit may be adapted to generate an alert message if the first person is determined either not to be wearing the device properly or to have the physical condition. The alert message includes information corresponding to the station identifier and the device identifier. The alert message may be sent to a predetermined recipient via a communication network to which the control unit is connectable. The communication network may be a public communication network.

The control unit may be further adapted to instruct the device to transmit its device identifier and a physiological parameter reading measured therewith. The control unit may instruct the device by broadcasting a corresponding instruction via at least one selected access station, the instruction being receivable by all devices in a coverage area of the at least one selected access station.

The system may further include at least one physiological parameter measuring device that is attachable to the first person for monitoring at least one physiological parameter of the first person. Each device has a device identifier and is being connected to the respective access station of the cell when it is within the cell.

According to another aspect of the invention, there is provided a physiological parameter measuring device. The device includes a transducer, a transmitter and a processor. The processor is connected to the transducer and the transmitter. The processor is adapted to control the transducer to at least intermittently measure a physiological parameter of a person and to control the transmitter to transmit a reading corresponding to the measured physiological parameter when it is determined that the reading has deviated from at least a predetermined threshold.

The device may further include a receiver connected to the processor and wherein the reading is also transmitted if the processor receives an instruction to do so via the receiver.

The device may further include a housing including a first portion, a second portion and a flexible medial portion connected between the first and the second portion. The device may be a thermometer for measuring the temperature of a person. The processor, transmitter and receiver may be accommodated within the first housing portion and the transducer may be supported on the second housing portion.

The first and the second portion may be bent towards each other to define a U-shaped device for hooking on a piece of clothing so that the transducer is in contact with the abdomen of a person for measuring a temperature thereat.

BRIEF DESCRIPTION OF DRAWINGS

The invention will be better understood with reference to the drawings, in which:

FIG. 1 is a schematic drawing of a system for capturing at least one physiological parameter and movement within an area of at least one person according to an embodiment of the invention, wherein the system includes a number of access stations connected to a control unit;

FIG. 2 is a drawing showing tables of records stored in the control unit of FIG. 1;

FIG. 7 is a flowchart showing a sequence for determining a temperature correction factor; and FIG. 8 is a flowchart showing a sequence for determining an individual threshold for a person.

DETAILED DESCRIPTION

Figure 3A:
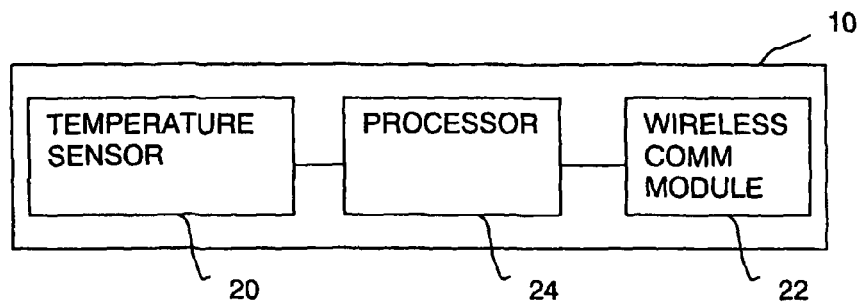
FIG. 3A is a schematic drawing showing a block diagram of a thermometer whose data transmission is receivable by the access stations in FIG. 1.

Hereafter, a preferred embodiment of the invention will be described in the context of a system for monitoring the body temperature of people who are mobile in a building. However, it is to be understood that the invention is usable in other physiological parameter monitoring systems for monitoring other physiological parameters, such as pulse rate, respiration rate, blood pressure, and blood glucose level, and even electrocardiogram signals of a group of people in a given area.

FIG. 1 is a block diagram of a system 2 for constantly monitoring the body temperature of a group of people in a building according to an embodiment of the present invention. The system 2 includes a remote control unit 4 and a number of access stations 6 connected to the control unit 4. The control unit 4 may be a server computer. The access stations 6 may be connected to the control unit 4 via a dedicated network or a local area network (LAN). The network may either be a wired network or a wireless network. An example of a wireless network is a network according to the IEEE 802.11b specifications. Each access station 6 in the system 2 has a unique station identifier (ID).

The access stations 6 are deployed to cover different locations of the building. The access stations 6 may be installed on the ceiling of each of the different locations. Each access station 6 has a range of operation that covers and thus defines a coverage area or cell 8. Each access station 6 includes a first interface (not shown) that allows the access station 6 to be connected to the network and a second interface (not shown) that allows the access station 6 to communicate with one or more temperature sensing devices or thermometers 10 that are within its cell 8. The first interface depends on the type of network. The second interface may be for supporting a wireless type of communication protocol, wherein the access station 6 may be able to simultaneously communicate with more than one thermometer 10. Examples of such a wireless type of communication protocol are the existing Bluetooth, wireless LAN, IEEE 802.11b protocols.

Alternatively, a self-defined wireless protocol using amplitude modulation, frequency modulation, phase modulation, diffused infrared or infrared signal modulation is also possible. When using for example the Bluetooth protocol, an access station 6 can communicate with up to seven thermometers 10 at the same time. An access station 6 using such a protocol has a coverage area 8 of a radius of about ten meters around the access station 6. In Bluetooth terms, the access station 6 is a master device and the thermometers 10 are slave devices.

Each thermometer 10 is able to at least intermittently transmit or broadcast a unique device identifier (ID) and a reading corresponding to a measured temperature as transmitted data. The access station 6 is able to pick up or receive the transmitted data, append its station ID to the data to form a data packet that is forwarded to the control unit 4. Each access station 6 and thermometers 10 within its coverage area 8 may be considered to form a piconet. When a thermometer 10 moves from a first cell 8 into a second cell 8, transmitted data of the thermometer will be received by an access station 6 of the first cell 8 and subsequently by another access station 6 of the second cell 8. The access station 6 of the second cell 8 would then send another data packet to the control unit 4. In this manner, the location of a thermometer 10 can be tracked based on the station ID of the access stations that receive the transmission of the thermometer 10 as the person moves about in the building.

At the control unit 4, each received data packet is stored as a record in a temperature information table 12 as shown in FIG. 2A. In addition to the device ID, station ID, and temperature reading, the time at which the packet is received are also included in the record 14. The time may also include a date. Such a temperature information table 12 is shown in FIG. 2A. The temperature information table 12 may be stored in any storage device (not shown), such as a hard disk, a floppy disk, a tape or the like, in the control unit 4. The control unit 4 is able to process, analyze, organize and present these records using software applications, an example of which will be described later.

The thermometers 10 are described in more details next. Each of the thermometers 10 includes a temperature sensor 20 and a wireless communication module 22 connected to a processor 24 as shown in FIG. 3A. The communication module 22 may include a transmitter (not shown) or a transceiver (not shown). The transceiver includes a transmitter and a receiver. Each thermometer 10 also includes a device ID that is readable by the processor. The device ID may be hardwired in the thermometer 10 or programmed therein. The thermometer 10 may or may not include a display (not shown). A thermometer 10 without a display is smaller and thus is likely to be more comfortable for wearing on a person's body. For such a thermometer without a display, the temperature reading may be transmitted to a Bluetooth-enabled mobile phone or PDA carried by the person for display thereon. Alternatively, the reading may be simply displayed on a display screen (not shown) of the control unit 4 when the control unit 4 receives the data packet transmitted by the thermometer 10.

The temperature sensor 20 is any transducer that is able to convert a temperature to a corresponding electrical signal. An example of such a transducer is a thermistor assembly. The processor 24 includes an internal analog-to-digital (A/D) converter with associated software (not shown) that converts the electrical signal to a temperature reading. The wireless communication module 22 is able to, under the control or direction of the processor 24, transmit the temperature reading and its device ID in a data packet. The thermometer 10 at least intermittently measures a temperature and transmits the temperature reading. In other words, the thermometer can transmit data continuously, at intermittent intervals or at periodic intervals. In some embodiments, the thermometer 10 periodically, for example once every ten seconds, measures a temperature and transmits the temperature reading.

Figure 3B:
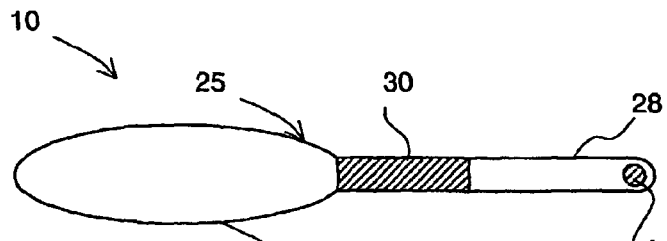
FIG. 3B is a drawing showing a plan view of a housing for the thermometer in FIG. 3A.
Figure 3C:
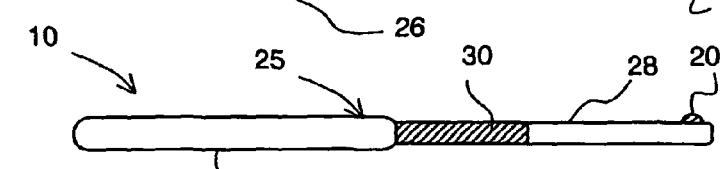
FIGS. 3C and 3D are drawings showing side views of the housing in FIG. 3A.
Figure 3D:
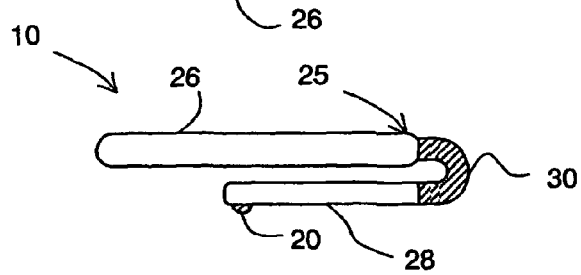

FIG. 3B shows a plan view of a housing 25 of the thermometer 10. FIGS. 3C and 3D are side views of the housing 25 of thermometer 10, shown in a straight and a bent position respectively. The housing 25 has a first body portion 26 for accommodating the processor 24 and the wireless communication module 22. The housing 25 has a second temperature sensing portion 28 that supports the temperature sensor 20. The temperature sensing portion 28 is connected to the body portion 26 via a flexible medial portion 30 that allows the thermometer 10 to be bent thereat. The flexible medial portion 30 may be of a resilient material, such as thermoplastic rubber, that allows the temperature sensing portion 28 to be bent over towards the body portion 26 to form a U shape. In this position of the thermometer 10, the temperature sensor 20 is outward facing.

Figure 3E:
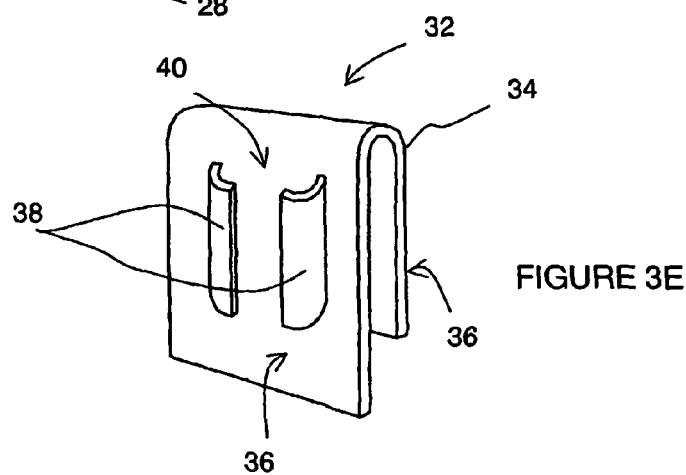
FIG. 3E is an isometric drawing of a holder for the thermometer shown in FIGS. 3B, 3C, and 3D.

During use for measuring the temperature at the abdomen of a person, a holder 32 made of a hard material, such as hard plastic, is provided for supporting the thermometer 10. FIG. 3E is a drawing of the holder 32. The holder 32 includes a clip 34 having two panels 36. On one panel 36 of the clip 34 are two protruding members 38 that define a pocket 40 for receiving the body portion 26 of the thermometer 10. On the other panel 36 of the clip is a catch (not shown) for receiving and holding the temperature sensing end 28 in place when the thermometer 10 is bent and placed in the holder 32. The clip 34 can be conveniently attached to a waist portion of a pair of pants so that the temperature sensor 20 is in contact with the abdomen of the person. In this position, the body portion 26 of the thermometer faces away from the person.

Figure 4:
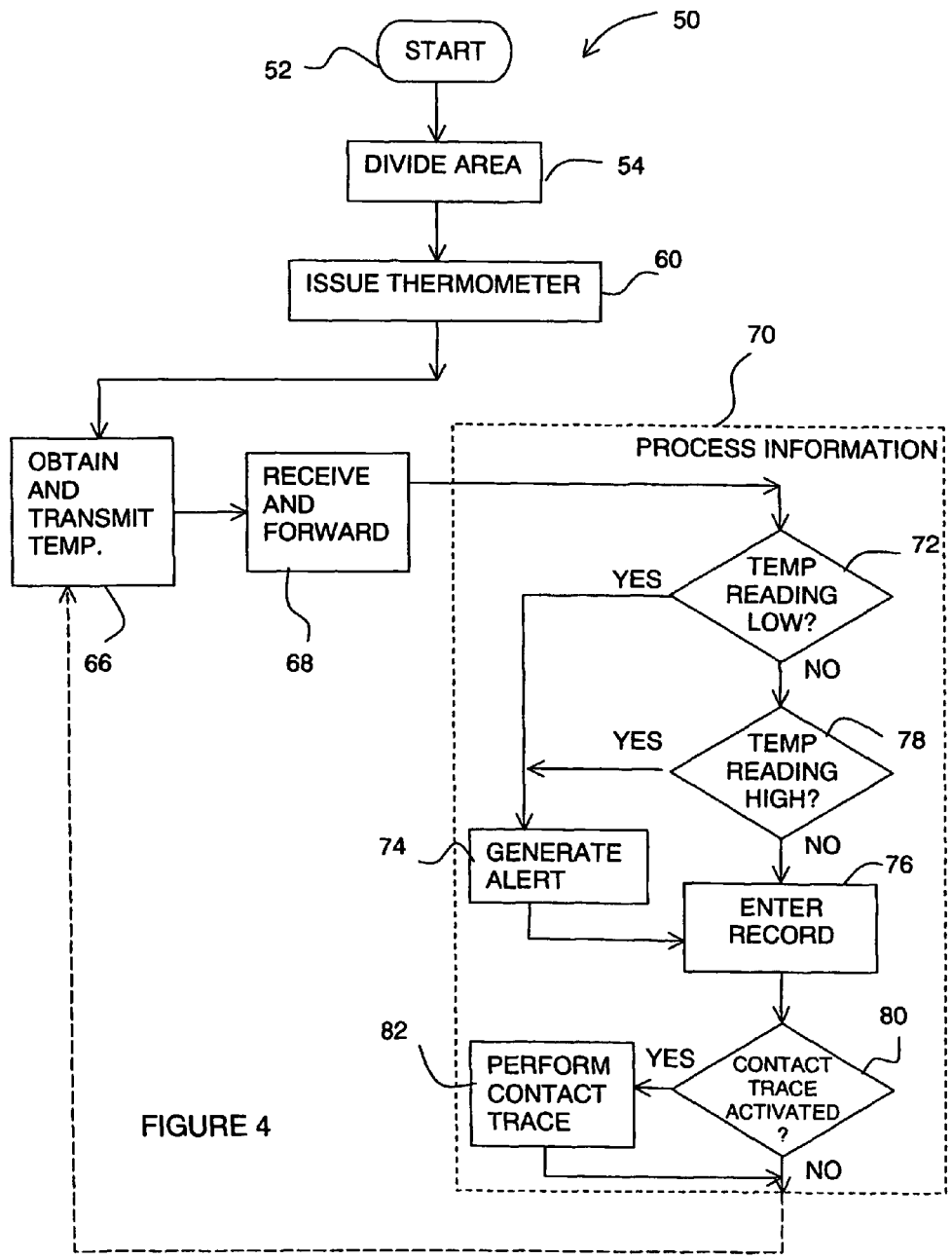
FIG. 4 is a flowchart showing a main sequence of steps for operating the system in FIG. 1.

The deployment of the system 2 for use in a building for tracking the movement and monitoring the temperature of a group of people in the building so that a person who is detected to have a physical condition, such as fever, can be located, is next described with the aid of FIG. 4. FIG. 4 shows a flowchart of a main sequence 50 of steps. The main sequence 50 starts in START step 52 and proceeds to a DIVIDE AREA step 54, wherein the access stations 6 are deployed at different locations of the building. With each access station 6 defining a cell 8, such a deployment serves to divide the building into identifiable cells 8. An operator enters the location where each access station 6 is deployed as a record 56 in a station location table 58 as shown in FIG. 2B. Each record 56 thus includes two fields—a station ID field and a location field. The station IDs of the access stations 6 serve as location IDs of the cells 8.

The main sequence 50 next proceeds to an ISSUE THERMOMETER step 60, wherein each person arriving at an entrance of the building is provided or issued with a thermometer 10. The device ID, name and contact details of the person issued with a thermometer 10 are entered as a record 62 into a name table 64 as shown in FIG. 2C. Each record 62 in this name table 64 therefore includes a device ID field, a name field and a contact details field. The person is made to wear the issued thermometer 10 such that his or her temperature may be at least intermittently taken using the thermometer 10.

The main sequence 50 next proceeds to an OBTAIN AND TRANSMIT TEMP step 66, wherein the thermometer 10 at least intermittently measures a temperature of the person and transmits a reading corresponding to the temperature along with its device ID.

The main sequence 50 next proceeds to a RECEIVE AND FORWARD step 68 when the person wearing the thermometer 10 enters a cell 8 adjacent to the entrance. An access station 6 serving the cell 8 receives the transmitted data of the thermometer 10. As described above, the access station 6 then forwards the data along with its station ID in a data packet to the control unit 4. In this manner, the reading and device ID becomes associated with the station ID.

The main sequence 50 next proceeds to PROCESS INFORMATION step 70 when the control unit 4 receives the data packet forwarded by the access station 6. With the information obtained in the data packet, it is possible for the control unit 4 to know the location of the person in the building at a cell level.

The details of how the information is processed in the control unit 4 are next described. The main sequence 50 upon entering the PROCESS INFORMATION step 70 proceeds to a TEMP READING LOW? decision step 72, wherein the control unit 4 determines if the temperature reading in the data packet is below a low-threshold value. If it is determined that the temperature reading is below the low-threshold value, the main sequence 50 proceeds to a GENERATE ALERT MSG step 74, wherein the control unit 4 generates a first alert message based on information collected from the various tables 12, 58, 64. The control unit 4 displays the first alert message on the display screen of the control unit 4. The control unit 4 may also send the first alert message to a selected recipient, such as the operator, via a communications network, such as a public paging or mobile communications network (not shown).

The TEMP READING LOW? decision step 72 may be used to detect if the thermometer 10 is properly worn on the person. In this case, the low-threshold value may be set to a temperature of for example 32° C., which is lower than the normal body temperature range of 36.5 to 37.2° C. If the thermometer 10 is not properly worn or becomes dislodged from the person, the temperature reading would fall below the low-threshold value. For such a condition, the first alert message may, for example, be "USAGE ALERT: Mr. A's temperature is 31.9° C. at 1:25 pm, 2 Apr. 2003. He's in Conference Room B." or simply "USAGE ALERT: Mr. A, who is in Conference Room B, may not be wearing his thermometer properly". An operator upon receiving such a message may then approach Mr. A to check and ensure that he is wearing his thermometer 10 properly. The main sequence 50 next proceeds to an ENTER RECORD step 76, which will be described shortly.

If it is determined in the TEMP READING LOW? decision step 72 that the temperature reading is not below the low-threshold value, the main sequence 50 proceeds to a TEMP READING HIGH? decision step 78, wherein the control unit 4 compares the temperature reading of the thermometer 10 with a high-threshold value to determine if the temperature reading is above the high-threshold value. The high-threshold value may be set at 38° C. If it is determined that the temperature reading exceeds the high-threshold value, the main sequence 50 proceeds again to the GENERATE ALERT MSG step 74. In the step 74, the control unit 4, recognizing from the station ID that the cell 8 is adjacent the entrance of the building, sends a second alert message to a security personnel stationed at the entrance to indicate that the person wearing the thermometer 10 has a higher than acceptable temperature. This second alert message may be "REFUSE ENTRY: Mr. A has a body temperature of 38.5° C.". The security personnel may respond to the second alert message by escorting the person away for the person to be more thoroughly examined by a doctor for example.

If it is determined in the TEMP READING HIGH? decision step 78 that the temperature reading of the thermometer 10 is equal or less than the high-threshold value, the control unit 4 will not send an alert message to the security guard. The main sequence 50 then proceeds to the ENTER RECORD step 76, wherein the control unit 4 creates a record in the temperature information table 12 from the received data packet. The control unit 4 updates a time field of the record with the time of receipt by the control unit 4 of the data packet so as to associate a time with the other fields of the record 14. That is, each record in the temperature information table includes a device ID, a temperature reading, a station ID and a time information. In this manner, the control unit 4 captures the data packet in a record.

When no second alert message is received by the security personnel at the entrance as determined by the steps 72, 78, the person is allowed to enter and roam in the building. The thermometer 10 will at least intermittently transmit a temperature reading and its device ID. The main sequence 50 will loop around the OBTAIN AND TRANSMIT step 66, the RECEIVE AND FORWARD step 68 and the PROCESS INFORMATION step 70 for each transmission by the thermometer 10 that is received by one of the access stations 6. Over time, the control unit 4 will create a large number of records in the temperature information table 12 for each of the thermometers 10. These records are thus available at a central location.

A scenario of the person moving into a Conference Room B in the building is next described. Let us assume that the person's temperature rises to 38.1° C. while in Conference Room B. The access station 6 covering Conference Room B will receive the temperature reading and device ID of the person's thermometer 10 and forward it to the control unit 4 as described above. The control unit 4 will detect that the person's temperature is above the high-threshold value in the TEMP READING HIGH? decision step 78. The control unit 4 will then generate a third alert message, such as "FEVER ALERT: Mr. A's temperature is 38.1° C. at 1:25 pm, 2 Apr. 2003. He's in Conference Room B" from data obtained from the tables 12, 58, 64. As with the case of the first alert message, the third alert message may be displayed on a display screen and/or sent to the operator. The operator upon receiving this third alert message may then inform the security personnel or a healthcare personnel to proceed to Conference Room B to escort Mr. A to a designated area so as to isolate him. In this manner, a person who has fever may be identified and located.

Figure 5:
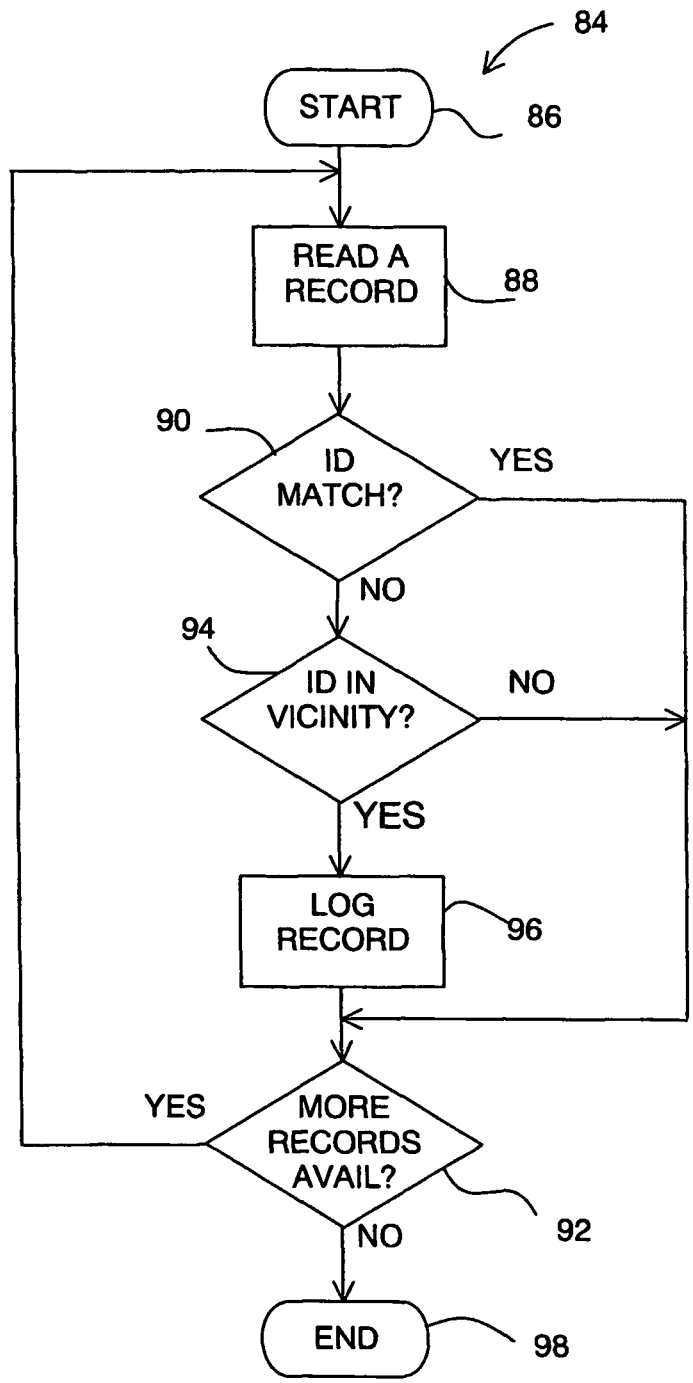
FIG. 5 is a flowchart showing a contact trace sequence that is implemented in the control unit of FIG. 1.

After the ENTER RECORD step 76, the main sequence 50 proceeds to a CONTACT TRACE ACTIVATED? decision step 80, wherein the control unit 4 determines if the operator has initiated the contact tracing application or feature. This contact tracing application may be automatically activated when a thermometer reading received by the control unit 4 is deemed to have exceeded the high-threshold value. Alternatively, the operator may initiate the feature with a selected record. If it is determined in this step 80 that the contact tracing feature is activated, the main sequence 50 proceeds to the PERFORM CONTACT TRACE step 82, wherein the control unit 8 performs contact tracing by following a contact tracing sequence 84 as shown in FIG. 5.

The contact trace sequence 84 is described next with the aid of FIG. 5. The contact trace sequence 84 starts in a START step 86, wherein the control unit 4 extracts the records in the temperature information table 12 that were collected over a period of time. The period of time may be the past 10 days. The contact trace sequence 84 then proceeds to a READ A RECORD step 88, wherein the control unit 4 reads a record from the extracted records. The contact trace sequence 84 then proceeds to an ID MATCH? decision step 90, wherein the control unit 4 determines if the device ID in the read record is equal to the device ID of the selected record. If it is determined that the IDs in the two records match, the contact trace sequence 84 proceeds to a MORE RECORDS AVAILABLE? decision step 92. If it is determined in the ID MATCH? decision step 90 that the device ID of the read record is not equal to the device ID of the selected record, the contact trace sequence 84 proceeds to an ID IN VICINITY? decision step 94, wherein the control unit 4 determines if the thermometer 10 having the device ID in the read record had been in the vicinity, or physical proximity, of the thermometer 10 having the device ID of the selected record. In one embodiment, the thermometer 10 having the device ID of the read record is considered to be in the vicinity of the thermometer 10 having the device ID in the selected record if the read record has the same station ID and about the same time as the selected record. In another embodiment, the thermometer 10 having the device ID of the read record is considered to be in the vicinity of the thermometer 10 having the device ID in the selected record if the read record has the same station ID and about the same time as any one of all the extracted records having the same device ID as the selected record.

If it is determined in this ID IN VICINITY? decision step 94 that the thermometer 10 from which the read record is obtained is not in physical proximity of the thermometer 10 having the device ID in the selected record, the contact trace sequence 84 proceeds to the MORE RECORDS AVAILABLE? decision step 92. If it is determined that the two thermometers were in the same vicinity, the contact trace sequence 84 proceeds to a LOG RECORD step 96, wherein the control unit 4 logs the read record into a contact tracing table (not shown). The contact trace sequence 84 next proceeds to the MORE RECORDS AVAILABLE? decision step 92, wherein the control unit 4 determines if there are still further records amongst the extracted records to be read. If it is determined that there are more records to be processed, the contact trace sequence 84 returns to the READ A RECORD step 88. Otherwise, the contact trace sequence 84 ends in an END step 98.

The control unit 4 uses the records in the contact tracing table, more specifically the device ID in the records, to access the name table 64 to generate a contact trace list (not shown). The contact trace list may also be displayed as messages on the display screen, such as "CONTACT TRACED: Mr. C is with Mr. A in Conference Room B at 1:25 pm, 2 Apr. 2003," if the selected record is the one that is processed to cause the generation of the third alert message described above. The operator who reads the messages can then act accordingly, such as to contact or to serve the people whose names appear in the contact trace list with quarantine orders.

In the system 2 above, the thermometer 10 is described to be intermittently or periodically transmitting data that is picked up by the access stations 6. Such intermittent or periodic transmission of data, especially those involving radio frequency transmissions, may consume significant battery power and drain the battery in a short period of time. It is therefore desirable to minimize the number of such transmissions by the thermometers 10 so as to conserve battery power.

Figure 6A:
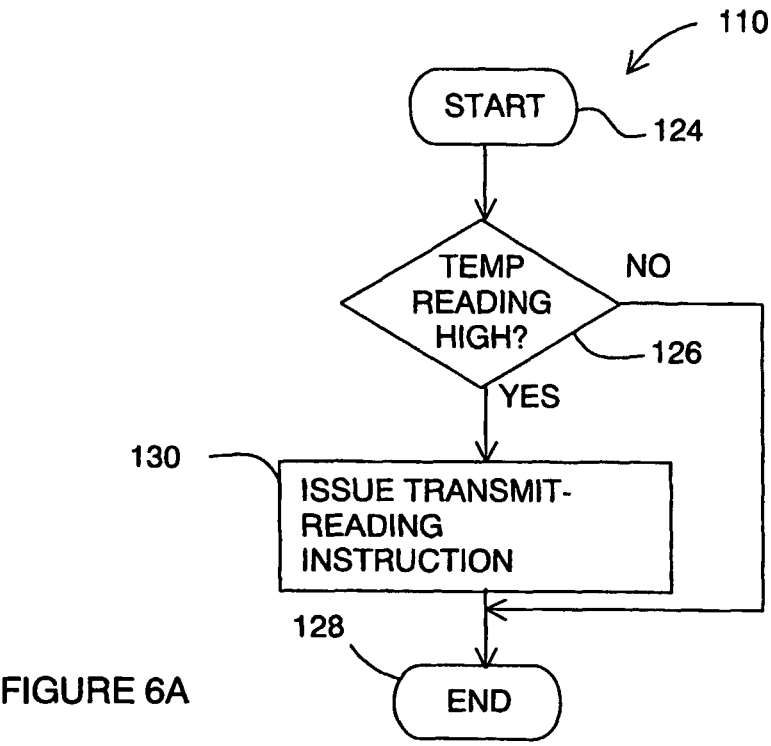
FIGS. 6A and 6B are flowcharts showing a sequence implemented in a a control unit and a thermometer respectively for reducing data transmission of the thermometer.
Figure 6B:
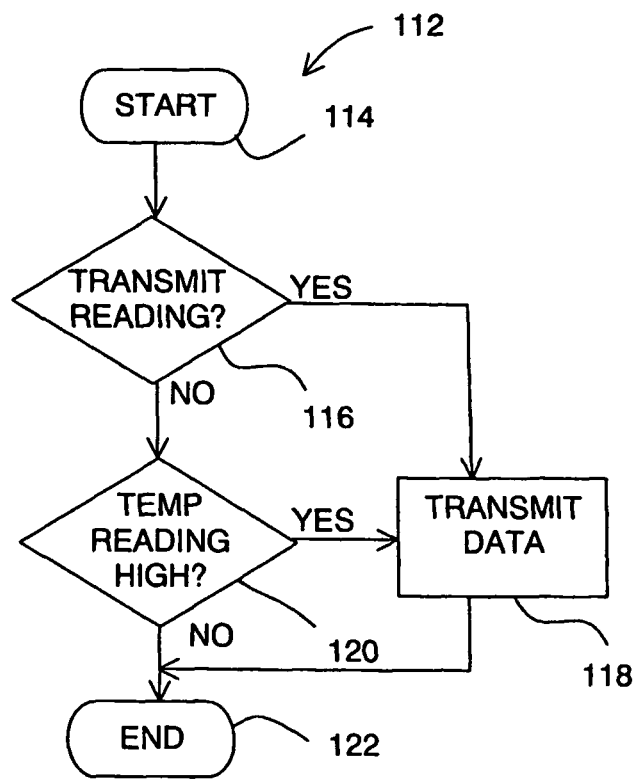

One method of minimizing the number of transmissions will be described with the aid of flowcharts in FIGS. 6A and 6B, which show a master sequence 110 and a slave sequence 112 implemented in the control unit 4 and the thermometer 10 respectively.

The slave sequence 112 in the thermometer 10 starts in a START step 114, when a temperature reading is obtained. The slave sequence 112 next proceeds to the TRANSMIT READING? decision step 116, wherein the processor 24 determines if a transmit-reading instruction from the control unit 4 has been received previously by the thermometer 10. If it is determined that the transmit-reading instruction is received, the slave sequence 112 proceeds to a TRANSMIT DATA step 118, wherein the thermometer 10 transmits data as described above.

However, if it is determined that the transmit-reading instruction is not received, the slave sequence 112 proceeds to a TEMP READING HIGH? decision step 120, wherein the processor 24 compares the temperature reading with a transmit-threshold value. If it is determined that the temperature reading exceeds the transmit-threshold value, the slave sequence proceeds to the TRANSMIT DATA step 118 to transmit data as described above. After the TRANSMIT DATA step 118, the slave sequence 112 ends in an END step 122. If it is determined that the temperature reading is equal or below the transmit-threshold value, the slave sequence 112 proceeds to the END step 122 without the thermometer 10 transmitting any data. With such a sequence of operation, the thermometer 10 transmits data only when a person is suspected of running a temperature, i.e. having a fever. The transmit-threshold value may be set to be equal or slightly lower than the high-threshold value. For simplicity, the transmit-threshold value may be set to a fixed value for all people. As an example, the transmit-threshold value may be set to 37.5° C. if the high-threshold value is set to 38° C.

The corresponding master sequence 110 in the control unit 4 is next described. The master sequence starts in a START step 124, wherein the control unit 4 receives a temperature reading, a device ID, and a station ID from an access station 6 as described above. The master sequence 110 next proceeds to a TEMP READING HIGH? step 126, wherein the control unit 4 compares the temperature reading with the transmit-threshold value. If it is determined that the temperature reading does not exceed the transmit-threshold value, the master sequence 110 ends in an END step 128.

If however, it is determined in the TEMP READING HIGH? decision step 126 that the temperature reading exceeds the transmit-threshold value, the master sequence 110 proceeds to an ISSUE TRANSMIT-READING INSTRUCTION step 130, wherein the control unit 4 directs the access station 6 through which the temperature reading is received to broadcast a transmit-reading instruction that is receivable by the thermometers 10 in its cell 8. Alternatively the control unit 4 may direct other access stations 6 or all access stations 6 to transmit the transmit-reading instruction. The master sequence 110 next proceeds to the END step 128. In this manner the thermometers 10 that are in the cell 8 would be able to receive the transmit-reading instruction and accordingly transmit data.

A scenario is next described to illustrate the operation of the master and the slave sequences 110, 112. Suppose Mr. A is in Conference Room B together with Ms. X, Ms. Y and Mr. Z. At 1 pm, their body temperatures are all below the transmit-threshold value, which is set at 37.5° C. Accordingly, their thermometers 10 and the access station 6 in the Conference Room B do not transmit any data. Then at 1:25 pm, Mr. A's temperature is detected by his thermometer 10 to be at 37.6° C., i.e. higher than the transmit-threshold value of 37.5° C. Mr. A's thermometer 10 will then, according to the slave sequence 112, transmit data that contains the temperature reading and its device ID. The access station 6 picks up the transmission and forwards the transmitted data along with the station ID to the control unit 4 as described above. The control unit 4, according to the master sequence 110, detects that Mr. A's temperature is above the transmit-threshold value and sends a transmit-reading instruction to one or more access stations 6 covering Conference Room B. The thermometers 10 on Ms. X, Ms. Y and Mr. Z, who are in the Conference Room B will receive the transmit-reading instruction, and they will accordingly start to transmit their respective temperature readings and device IDs. The one or more access stations 6 will receive these transmissions and forward them to the control unit 4. With these transmitted data, the control unit 4 is able to capture data that shows who is in the vicinity or physical proximity of Mr. A at the moment when Mr. A's temperature is detected to exceed the transmit-threshold value.

It the system 2 is solely for locating a person suspected to run a temperature, i.e. have a fever, or to not be wearing his or her thermometer 10 properly, there is no need for the master and slave sequences 110, 112 described above. In such a case, the thermometer after obtaining a temperature reading compares it with a TH1 threshold value and a TH2 threshold value. If the temperature reading is determined to be higher than the TH1 threshold value or lower than the TH2 threshold value, the thermometer 10 will transmit data so that the control unit 4 is alerted. Otherwise, the thermometer 10 will not transmit any data. The TH1 threshold value may be the same as the high-threshold value of 38° C. and the TH2 threshold value may be the same as the low-threshold value of 32° C.

Another aspect of the above system 2 may be improved. This aspect relates to the accuracy of a temperature reading obtained from a person's abdomen. It is generally known that a temperature taken orally, that is by placing the temperature sensing end 28 of a thermometer 10 under a person's tongue, gives a reasonably accurate indication of the core body temperature of the person. However, the oral method is not appropriate for continuous temperature monitoring because it is both uncomfortable and inconvenient to have a thermometer 10 stuck in the mouth for a long period of time. There are certain parts of the human body, such as the armpit, abdomen or wrist, which are more comfortable and convenient for continuous temperature monitoring. However, measurement from these body parts usually does not give a reading that reflects the core body temperature. The temperature measured from these parts could be significantly lower (e.g., 0.5 to 3° C.) than that measured from the mouth. One usual practice is to add a correction factor, that is an average value obtained from the population, to the measured temperature obtained from a body part. For example, a correction factor of 0.5° C. may be added to the temperature measured from the armpit of 36.5° C. to give a temperature reading of 37° C., which is closer to the actual core body temperature. As the difference in temperature taken at the armpit and mouth varies from person to person, the use of a single common correction factor may not result in an accurate determination of the core body temperature. It is thus desirable to determine a temperature correction factor for each individual.

FIG. 7 shows a flowchart of a calibration sequence 132 for obtaining a correction factor for use in a thermometer 10 issued to a person. The calibration sequence 132 starts in a START step 134, when a calibration mode of the thermometer 10 is activated, for example by the person pressing a button (not shown) on the thermometer 10. The calibration sequence 132 next proceeds to a TAKE ORAL TEMPERATURE step 136, wherein the thermometer 10 prompts the person to place the thermometer 10 in his or her mouth beneath the tongue for the oral temperature to be taken. The prompt may be in the form of a lighted LED (not shown). The thermometer 10 may produce an alert signal, either audio or visual, to indicate that the oral temperature is taken and prompt the person to place the thermometer 10 at his or her abdomen for the abdomen temperature to be taken. The person would then place the thermometer 10 into the holder 32 and clip the holder 32 onto his or her pants as described above. At this point, the calibration sequence 132 proceeds to a TAKE ABDOMEN TEMPERATURE step 138, wherein the thermometer 10 measures the abdomen temperature. The calibration sequence 132 next proceeds to a CALCULATE CORRECTION FACTOR step 140, wherein the thermometer 10 calculates a correction factor based on the oral temperature and the abdomen temperature. The corrector factor may simply be the difference between the oral temperature and the abdomen temperature. The correction factor is stored in the thermometer 10.

The calibration sequence 132 ends in an END step 142, wherein the thermometer 10 exits the calibration mode and switches back to a temperature monitoring mode. In the temperature monitoring mode, the thermometer 10 after obtaining a temperature reading, adjusts it by including, for example by adding, the correction factor before transmitting it. In this manner, the adjusted temperature reading which is transmitted is closer to the core body temperature of the person. Such a calibration sequence 132 may be performed when the person is issued with the thermometer 10 at the entrance of a building or when the person is allowed entry into the building after the person is initially determined to be without a fever.

A further aspect of the system 2 may be improved. This further aspect relates to the high-threshold value used for determining if a person has fever. The system 2 is described above to have a single common high-threshold value for all people. Since the normal temperature varies from person to person, it may be desirable to determine a high-threshold value for each individual person.

One way of determining a personal high-threshold value is by statistically computing the high-threshold value using the most recently obtained temperature readings of a person.

These most recently measured temperature readings may either be stored in the thermometer 10 or in the control unit 4.

A threshold determination sequence 150 in the thermometer 10 for statistically computing a high-threshold value for a person is next described with the aid of FIG. 8. The threshold determination sequence 150 starts in a START step 152, when a person presses a button (not shown) on the thermometer 10 and then wears the thermometer 10. The method proceeds to a PERIODIC MEASUREMENT step 154, wherein the thermometer 10 periodically, for example once every ten seconds, takes and stores a temperature reading of the person. The sequence 150 next proceeds to an ENOUGH DATA COLLECTED? decision step 156, wherein the thermometer 10 determines if the number of temperature readings has reached a predetermined number. If it is determined in this step 156 that the number of temperature readings is below the predetermined number, the sequence 150 loops around the ENOUGH DATA COLLECTED? decision step 156 waiting for the number of readings taken to reach the predetermined number, such as one hundred readings. When the number of readings reaches the predetermined number, the sequence 150 exits the ENOUGH DATA COLLECTED? decision step 156 and proceeds to COMPUTE HIGH_THRESHOLD step 158. In this step 158, the processor 24 in the thermometer 10 may calculate the high-threshold value for the person using the following formula:

$$\text{high-threshold value} = \mu + k\sigma,$$

wherein $\mu$ is the mean and $\sigma$ is the standard deviation of the predetermined number of readings, and k is a positive number.

If the collected temperature readings are normally distributed and if k=3, 99.9% of the temperature readings will then be less than the high-threshold value computed according to the formula above.

Alternatively, the high-threshold value may simply be set to be a sum of a maximum value in the temperature readings and a margin value of for example 0.5° C. As an example, the maximum value of the predetermined number of temperature readings is 37.5° C. and the resultant high-threshold value would be 38° C. A single temperature reading may also be used to determine the high-threshold value.

The high-threshold value may be entered into the control unit 4 by the operator or it may be transmitted to the control unit 4 via the access station 6 using a designated data packet. If the control unit 4 receives such a high-threshold value from a thermometer 10, the control unit 4 would use this high-threshold value for future comparison in the TEMP READING HIGH? decision step 78 in the main sequence 50, otherwise the control unit 4 simply uses the default common high-threshold value available in the control unit 4. The threshold determination sequence 150 ends in an END step 160.

It should be noted that the method of determining a high-threshold value just described is also applicable for determining the other above-mentioned threshold values, such as the low-threshold value, the transmit-threshold value, the TH1 and TH2 threshold values.

It should also be noted that the method of determining a high-threshold value may be performed on the control unit 4 instead of the thermometers 10. In such a case, the high-threshold value may be a single common high-threshold value that is determined based on the temperature readings received from all thermometers 10 whose readings are captured by the control unit 4.

Although the invention is described as implemented in the above-described embodiment, it is not to be construed to be limited as such. For example, it is not necessary for the system to include multiple access stations 6. A system including only a single access station 6 will also work. In such a case, the access station 6 may be integrated with the control unit 4. That is, the access station 6 communicates with the control unit 4 via internal buses rather than through a physical communication link. Such a system may be deployed at "check points", such as at entrances to buildings, offices, hospitals, and at immigration check points of airports or border crossings. When so deployed, the system is used not so much for tracking the location of people but merely for "scanning" the body temperature of people passing through these check points. A person going through one of these check points is required to have his or her temperature taken using the thermometer as described above. The reading of the thermometer will be transmitted to the access station. The control unit in turn receives the temperature reading via the access station. If the reading is determined by the control unit to be above a predetermined high-threshold value, the person may be refused entry so that remedial action may be taken, such as getting the person to consult a doctor and placing the person under quarantine.

As another example, a system for home application may include a Bluetooth-enabled mobile phone or personal digital assistant (PDA) as a control unit. In such a case, a Bluetooth repeater is used as an access station. The Bluetooth repeater is a device that simply re-transmits the signal that it receives. The thermometer in such a system includes a Bluetooth transceiver.

As yet another example, the thermometer may further include a panic button that may be actuated for the thermometer to transmit an emergency request for medical attention that includes the device ID of the thermometer. An access station in the vicinity of the thermometer receives the transmitted emergency request and forwards it together with its station ID to the control unit. The control unit upon receiving the emergency request displays a message on the display screen. The message may be "WARNING: Mr. A, who is in Conference Room B, requires immediate attention. Message logged at 1:25 pm, 2 Apr. 2003." The operator can then summon healthcare personnel to attend to Mr. A immediately.

As yet a further example, the thermometer, which contains a unique device ID, can also double up as a security access device. For example, when a person who carries a thermometer approaches the entrance to a secured area, an access station at the entrance could authenticate the device ID and allow or deny access to the person accordingly.

As yet another further example, dividing an area into cells may involve deploying a transmitter in each of several locations of a building. Each transmitter is adapted to transmit a respective location identifier as a beacon. As each device moves into a location, the device is able to receive the transmitted location identifier and associate it with a reading and a time at which the reading is obtained using the device. The associated reading, time and location identifier may be transmitted by the device to a remote location each time a reading is obtained. Alternatively, the associated reading, time and location identifier, along with the device identifier may be stored in the device for uploading to a remote location at a later time. Although the latter implementation does not allow immediate detection, identification and location of a person having a physical condition, the data collected and stored in the device allows those who have been in physical proximity with the person at about the time when the person develops the physical condition to be subsequently identified. The data may also be used for identifying those who have been in physical proximity with the person a selected period of time prior to the person being detected only subsequently to have a physical condition. The location identifier may also be information recorded on a tag at each location of the building. In such a case, the thermometer may be used to read the tag. If the thermometer is used as a security access device as described above, the location identifier may be transmitted to the thermometer when it is used for gaining access to each location.

We claim:

1. A method of capturing and monitoring at least one physiological parameter and movement within an area of a group of at least one person, the method comprising:
    dividing the area into cells, each having a unique location identifier by providing a plurality of access stations in a spatial arrangement within the area, thereby dividing the area into cells;
    providing each person with a device for measuring at least one physiological parameter of the person, each device having a unique device identifier and the at least one physiological parameter being indicative of whether the person has a physical condition;
    at least intermittently measuring a physiological parameter of each person using the device provided to the person, to obtain a physiological parameter reading for each measurement;
    transmitting, by the device, a physiological parameter reading obtained by the device and the device identifier of the device;
    receiving the transmitted physiological parameter reading and device identifier by the access station of the cell in which the physiological parameter reading is obtained;
    associating each physiological parameter reading with the device identifier of the device by which, the location identifier of the cell in which, and a time at which the physiological parameter reading is obtained; and
    storing, as a record, each physiological parameter reading and its associated device identifier, location identifier, and time;
    comparing the physiological parameter reading of at least one record with a physiological parameter threshold value to determine whether any person of the group of at least one person has a physical condition;
    identifying and locating a person having the physical condition on the basis of the device identifier and the location identifier; and
    determining whether there are further persons of the group of at least one person in a vicinity of a person having the physical condition, by comparing the location identifier and time of the record of the person having the physical condition with the location identifier and time of each of at least one further record.

2. The method according to claim 1, further comprising transmitting a physiological parameter reading and its associated device identifier, location identifier, and time to a remote location prior to storing them at the location.

3. The method according to claim 1, comprising comparing each physiological parameter reading with a first predetermined physiological parameter threshold value to determine whether the person wearing the device by which the reading is obtained, is wearing the device properly.

4. The method according to claim 3, further comprising generating an alert message indicating the identity and location of the person, if the person is determined not to be wearing the device properly.

5. The method according to claim 1, further comprising comparing each physiological parameter reading with a second physiological parameter threshold value to determine whether the person wearing the device by which the reading is obtained, has a physical condition.

6. The method according to claim 5, further comprising generating an alert message indicating the identity and location of the person, if the person is determined to have the physical condition.

7. The method according to claim 6, further comprising:
    matching a time and location identifier associated with at least one physiological parameter reading obtained by a device of at least one other person with those of the identified and located person, and
    identifying the at least one other person to have been in physical proximity to of the identified and located person if there is a match.

8. The method according to claim 5, wherein the second predetermined physiological parameter threshold value is predetermined individually.

9. The method according to claim 1, further comprising transmitting, by an access station, a physiological parameter reading and its associated device identifier, location identifier, and time.

10. A system for capturing and monitoring at least one physiological parameter and movement within an area of a group of at least one person, the system comprising:
    a remote control unit; and
    a plurality of access stations provided in a spatial arrangement within the area, thereby dividing the area into cells;
    wherein each access station is associated with a cell, has a unique location identifier, is connected to the control unit, and is configured to receive, from a physiological parameter device attached to a person in the cell, a physiological parameter reading obtained by the device and a unique device identifier of the device;
    wherein the received physiological parameter reading, the received device identifier, the location identifier of the access station, and a time at which the physiological parameter reading is obtained, are transmitted by the access station to the control unit and stored as a first record at the control unit, said physiological parameter reading, device identifier, location identifier, and time being associated with each other;
    wherein the control unit is configured to compare the physiological parameter reading of at least one record with a physiological parameter threshold value to determine whether any person of the group of at least one person has a physical condition;
    wherein the control unit is further configured to identify and locate a person having the physical condition on the basis of the device identifier and the location identifier;
    wherein the control unit is further configured to determine whether there are further persons of the group of at least one person in a vicinity of a person having the physical condition, by comparing the location identifier and time of the record of the person having the physical condition with the location identifier and time of each of at least one further record.

11. The system according to claim 10, further comprising at least one physiological parameter measuring device that is attachable to each person for measuring at least one physiological parameter of the person, each device having a unique device identifier and being in communication with the access station of a cell when it is within the cell.

12. The system according to claim 10, wherein the control unit is further configured to provide information corresponding to the device identifier and the location identifier that are associated with each physiological parameter reading, for identifying and locating the person having the physical condition.

13. The system according to claim 11, wherein each physiological parameter measuring device comprises:
   a transducer;
   a transmitter; and
   a processor connected to the transducer and the transmitter, wherein the processor is configured to control the transducer in such a way that the transducer at least intermittently measures a physiological parameter of a person and to control the transmitter in such a way that the transmitter transmits a reading corresponding to the measured physiological parameter.

14. The system according to claim 13, wherein the physiological parameter measuring device is adapted to be attached to a person such that it is capable of measuring a physiological parameter at the abdomen of the person.

15. The system according to claim 10, wherein the physiological parameter measured is a body temperature of a person, and wherein a physiological parameter correction factor is determined from the difference between an oral temperature and an abdomen temperature of the person.

16. A system for capturing and monitoring at least one physiological parameter and movement within an area of a group of at least one person, the system comprising:
   a remote control unit;
   a plurality of access stations provided in a spatial arrangement within the area, thereby dividing the area into cells, wherein each access station is associated with a cell, has a unique location identifier, and is connected to the control unit; and
   at least one physiological parameter measuring device that is attachable to each person for measuring at least one physiological parameter of the person to obtain a physiological parameter reading for each measurement, each device having a unique device identifier and being in communication with the access station of a cell when it is within the cell;
   wherein each physiological parameter measuring device is configured to transmit a physiological parameter reading obtained by the device and the device identifier of the device;
   wherein the access station of each cell is configured to receive the transmitted physiological parameter reading and device identifier of a device, if the device is within the cell, and to transmit the received physiological parameter reading, the received device identifier, the location identifier of the access station, and a time at which the physiological parameter reading is obtained, to the control unit, said physiological parameter reading, device identifier, location identifier, and time being associated with each other;
   wherein each physiological parameter reading and its associated device identifier, location identifier, and the time are stored as a record at the control unit; and
   wherein the control unit is configured to
   (a) compare the physiological parameter reading of at least one record with a physiological parameter threshold value to determine whether any person of the group of at least one person has a physical condition;
   (b) identify and locate a person having the physical condition on the basis of the device identifier and the received location identifier; and
   (c) determine whether there are further persons of the group of at least one person in a vicinity of a person having the physical condition, by comparing the location identifier and time of the record of the person having the physical condition with the location identifier and time of each of at least one further record.

17. The system according to claim 16, wherein each physiological parameter measuring device comprises:
   a transducer;
   a transmitter; and
   a processor connected to the transducer and the transmitter, wherein the processor is configured to control the transducer in such a way that the transducer at least intermittently measures a physiological parameter of a person and to control the transmitter in such a way that the transmitter transmits a reading corresponding to the measured physiological parameter.

18. The system according to claim 16, wherein the physiological parameter measured is a body temperature of a person, and wherein a physiological parameter correction factor is determined from the difference between an oral temperature and an abdomen temperature of the person.

19. A method of capturing and monitoring at least a physiological parameter comprising body temperature and movement within an area of a group of at least one person, the method comprising:
   dividing the area into cells, each having a unique location identifier, by providing a plurality of access stations in a spatial arrangement within the area, thereby dividing the area into cells;
   providing each person with a device for measuring at least one physiological parameter of the person, each device having a unique device identifier and the at least one physiological parameter being indicative of whether the person has a physical condition;
   at least intermittently measuring a physiological parameter of each person using the device provided to the person, to obtain a physiological parameter reading for each measurement;
   transmitting, by the device, a physiological parameter reading obtained by the device and the device identifier of the device;
   receiving the transmitted physiological parameter reading and device identifier, by the access station of the cell in which the physiological parameter reading is obtained;
   adjusting the physiological parameter reading on the basis of a physiological parameter correction factor, the correction factor being determined from a difference between an oral temperature and an abdomen temperature;
   associating each adjusted physiological parameter readings with the device identifier of the device by which, the received location identifier of the cell in which, and a time at which the physiological parameter reading is obtained; and
   storing each adjusted physiological parameter reading and its associated device identifier, location identifier, and time.

20. A system for capturing and monitoring at least a physiological parameter comprising body temperature and movement within an area of a group of at least one person, the system comprising
   a remote control unit;
   a plurality of access stations provided in a spatial arrangement within the area, thereby dividing the area into cells, wherein each access station is associated with a cell, has a unique location identifier, and is connected to the control unit; and
   at least one physiological parameter measuring device that is attachable to each person for measuring at least one physiological parameter of the person to obtain a physiological parameter reading for each measurement, each device having a unique device identifier and being in communication with the access station of a cell when it is within the cell;

wherein each physiological parameter measuring device is configured to transmit a physiological parameter reading obtained by the device and the device identifier of the device;

wherein the access station of each cell is configured to receive the transmitted physiological parameter reading and device identifier of a device, if the device is within the cell, and to transmit the received physiological parameter reading, the received device identifier, the location identifier of the access station, and a time at which the physiological parameter reading is obtained, to the control unit, said physiological parameter reading, device identifier, location identifier, and time being associated with each other;

wherein each physiological parameter reading is adjusted on the basis of a physiological parameter correction factor, the correction factor being determined from a difference between an oral temperature and an abdomen temperature; and wherein each adjusted physiological parameter reading and its associated device identifier, location identifier, and time are stored as a record at the control unit.

* * * * *

UNITED STATES PATENT AND TRADEMARK OFFICE
CERTIFICATE OF CORRECTION

| | | |
|---|---|---|
| PATENT NO. | : 8,795,168 B2 | Page 1 of 1 |
| APPLICATION NO. | : 10/564493 | |
| DATED | : August 5, 2014 | |
| INVENTOR(S) | : Zenton Goh | |

It is certified that error appears in the above-identified patent and that said Letters Patent is hereby corrected as shown below:

In the Specification

Column 11, line 45: "It" should be -- If --.

Signed and Sealed this
Fourth Day of November, 2014

Michelle K. Lee
*Deputy Director of the United States Patent and Trademark Office*